United States Patent [19]
Berg et al.

[11] 3,932,469

[45] Jan. 13, 1976

[54] CITRACONIC ANHYDRIDE PROCESS

[75] Inventors: Rudolph G. Berg, Groton; Bryce E. Tate, Neantic, both of Conn.

[73] Assignee: Pfizer Inc., New York, N.Y.

[22] Filed: June 3, 1974

[21] Appl. No.: 475,770

[52] U.S. Cl.......................... 260/346.8 R; 260/386.8
[51] Int. Cl.².................................. C07D 307/60
[58] Field of Search............... 260/346.8 R, 346.8 A

[56] References Cited

UNITED STATES PATENTS 3,017,417  1/1962  Harkes............................ 260/346.8

*Primary Examiner*—Harry I. Moatz
*Attorney, Agent, or Firm*—Connolly and Hutz

[57]  ABSTRACT

The preparation of citraconic anhydride by catalytic vapor phase oxidation of methyl butanols and methyl butenols.

8 Claims, No Drawings

CITRACONIC ANHYDRIDE PROCESS

BACKGROUND OF THE INVENTION

This catalytic relates to the preparation of citraconic anhydride by the catalyst vapor phase oxidation of certain alcohols.

Citraconic anhydride is useful as a curing agent for epoxy resins, and is readily converted into itaconic acid, a valuable ingredient in numerous commercial resins.

Prior methods for the preparation of citraconic anhydride include the vapor phase catalytic decarboxylation and dehydration of citric and related 6-carbon acids (U.S. Pat. No. 3,701,805) as well as the vapor phase catalytic oxidation of olefinic hydrocarbons such as cracked naphtha (U.S. Pat. No. 2,719,853) and isoprene (U.S. Pat. No. 3,503,999).

SUMMARY OF THE INVENTION

It has now been found that citraconic anhydride can be prepared by the vapor oxidation of methyl butanols and methyl butenols at a temperature of from about 250° to 500°C. in the presence of vanadium oxide catalyst.

DETAILED DESCRIPTION OF THE INVENTION

In the practice of this invention, a gaseous stream containing a methyl butanol or methyl butenol and oxygen is passed over or through vanadium oxide catalyst at a temperature of between 250° and 500°C.; citraconic anhydride is formed and may be recovered from the exit stream.

The methyl butanols convertible to citraconic anhydride by this process include 2-methyl-1-butanol, 2-methyl-2-butanol (t-amyl alcohol), 2-methyl-3-butanol and 2-methyl-4-butanol, while the methyl butenols include 2-methylene-1-butanol, 2-methyl-2-buten-1-ol, 2-methyl-3-buten-1-ol, 2-methyl-3-buten-2-ol, 3-methyl-2-buten-1-ol, 3-methyl-3-buten-1-ol and 3-methyl-3-buten-2-ol. Preferred alcohols include 2-methyl-2-butanol, 3-methyl-3-buten-1-ol and especially 2-methyl-3-buten-2-ol. The alcohol starting material need not be pure, but for best results a purity of about 65 to 100 percent is desirable, a purity above about 90 percent being preferred. Mixtures of the isomeric alchols, such as may occur in the synthesis of these materials, may be used without separation.

The catalyst can be vanadium oxide or vanadium oxide admixed with one or more of the oxides of phosphorus, boron, copper, silver, chromium, molybdenum or tungsten, or compounds of these elements convertible to the oxide under the oxidation reaction conditions. The catalyst can be self-supporting or can be deposited on any of those supports, such as alundum, alumina, corundum, carborundum, silica, zirconia or pumice, which are commonly used for vapor phase oxidation catalysts. The active catalyst content of supported catalysts is generally about 2 to 50 percent of the total catalyst weight, about 5 to 25 percent being preferred. The vanadium oxide content of the active portion of mixed catalysts is normally about 50 to 99 percent. Standard methods of preparation of these catalysts, either unsupported or supported, are well known in the art and can be used.

The oxidation can be conducted at temperatures ranging from about 250°C. to about 500°C., with the preferred temperature being about 320°–420°C. Temperatures below 250°C. require unduly long contact times, while temperatures above 500°C. demand uncontrollably short contact times with resultant possible degradation of reactant and product. Although the reaction is normally, and preferably, conducted at atmospheric pressure, both reduced and superatmospheric pressures may be employed. Suitable pressures may range from about 0.5 to 5 atmospheres.

The contact time for the oxidation depends upon the temperature, the higher the temperature the shorter the period of contact. Operable times are readily determined by experiment. Best results are usually obtained between about 0.2 and 5 seconds, with the time at the preferred temperature of 320°–420°C. generally being about 1-2 seconds.

The concentration of alcohol vapor in the gas stream may vary over a wide range. Excellent results are usually obtained at concentrations between about 0.1 and 5 volume percent. Concentrations below 0.1 percent may result in uneconomically high costs from the large throughputs required and in lowered product recovery from the exit stream, while concentrations above 5 percent may cause reduced conversion and reduced selectivity. The preferred concentration for most economical operation is about 0.5–2 percent.

Preferred limits for the oxygen content of the gas stream are from about 5 to 50 percent by volume. Concentrations below 5 percent produce a definite drop in selectivity, while concentrations above 50 percent ate extremely exothermic and may be hazardous. Although the oxygen source can be an admixture of oxygen with any inert gas, such as nitrogen, carbon dioxide or water, the preferred source is air.

The product citraconic anhydride may be recovered as such from the exit gases by condensation or recovered as citraconic acid by water scrubbing of the exit gas stream.

The following examples are merely illustrative and are not to be construed as limiting the invention, the scope of which is defined by the appended claims. In these examples, all temperatures are in degrees centigrade (°C.), all vapor concentrations are in molar, or volume, percent, and all yields are stoichiometric yields. While, for convenience, the recorded temperature in these examples is that of the thermostated air bath, this temperature is considered to closely approximate the actual reaction temperature.

EXAMPLE 1

To a solution of 2.0 g oxalic acid in 20 cc water was added 1.17 g ammonium metavanadate and 0.11 g ammonium molybdate. About 4 g of a 20-40 mesh fraction of a crushed "Macroport" type LA 40 alundum catalyst carrier available from the Norton Company was treated with just enough of the above solution to uniformly moisten the carrier. The resulting mixture was dried on a steam bath with occasional mixing to insure uniformity, and the dried mixture was calcined at 450°–500°C. for 5 hours to yield a catalyst estimated to contain the active metal oxides in amounts equivalent to 4.0 percent $V_2O_5$ and 0.23 percent $MoO_3$. A reactor consisting of an ⅛ inch OD × 40 inches long aluminum tube having a wall thickness of 0.025 inch was wound in a tight coil, filled with the catalyst and placed into a heated thermostated air bath.

Air at the rate of 35 cc/min was continuously fed into the reactor while 2-methyl-3-buten-2-ol was metered into the stream at the rate of 1.9 μl/min using a constantly driven syringe. Under these conditions, the vapor mixture contained 1.26 molar percent starting alcohol and contacted the catalyst for about 1.8 seconds. The effluent gases from the reactor were monitored using a vapor fractometer. The temperature of the air bath was adjusted to give optimum yield of citraconic anhydride. Stoichiometric yields of 26% citraconic anhydride and 7% maleic anhydride were observed at an optimum air bath temperature of 380°–390°C.

EXAMPLE 2

The procedure of Example 1 was repeated substituting, individually, 3-methyl-3-buten-1-ol, 2-methyl-1-butanol, 2-methyl-2-butanol, 2-methyl-3-butanol or 2-methyl-4-butanol for the 2-methyl-3-buten-2-ol. The results of these experiments are tabulated below:

| starting alcohol | vapor conc. (%) | contact time (sec.) | bath temp. (°C.) | stoic. yield (%) citraconic anhydride | maleic anhydride |
|---|---|---|---|---|---|
| 3-methyl-3-buten-1-ol | 1.3 | 1.8 | 380–400 | 13 | 7 |
| 2-methyl-1-butanol | 1.24 | 1.8 | 370–390 | 10 | 26 |
| 2-methyl-2-butanol | 1.24 | 1.8 | 410–420 | 18 | 11 |
| 2-methyl-3-butanol | 1.24 | 1.8 | 380–390 | 14 | 7 |
| 2-methyl-4-butanol | 1.24 | 1.8 | 360–370 | 11 | 6 |

Citraconic anhydride may be similarly produced when 2-methylene-1-butanol, 2-methyl-2-buten-1-ol, 2-methyl-3-buten-1-ol, 3-methyl-2-buten-1-ol or 3-methyl-3-buten-2-ol is used as the starting alcohol.

EXAMPLE 3

A catalyst was prepared by fusing a mixture of 30 g vanadium pentoxide and 1 g cupric oxide, allowing the melt to cool and solidify, and then crushing and screening the resultant product to provide a 20–40 mesh fraction. The catalyst was charged to an 1/8 inch OD × 40 inches long tightly coiled aluminum tube as in Example 1 except the tube was only half filled with the catalyst. The tube was then placed into a thermostated air bath in such a manner that any feed stream entering the tube passed first through the empty end of the tube and then through the portion filled with catalyst. Air at the rate of 35 cc/min was continuously fed into the reactor while 3-methyl-3-buten-1-ol was metered into the stream at the rate of 1.9 $\mu$l/min using a constantly driven syringe. Under these conditions the vapor mixture contained about 1.3 molar percent starting alcohol and contacted the catalyst for about 0.9 second. The effluent gases from the reactor were monitored using a vapor fractometer. Citraconic anhydride was observed in 13% stoichiometric yield at a reaction temperature of 320°–360°C.

When the flow of air and feed of 3-methyl-3-buten-1-ol were adjusted to give a vapor mixture containing 0.22 percent alcohol, a 1.9 second contact time, and a 280°–300°C. reaction temperature, a 9% yield of citraconic anhydride was observed.

Adjusting the flow of air and feed rate of 3-methyl-3-buten-1-ol to give a vapor mixture containing 2.7 percent alcohol, a contact time of 0.9 second, and a reaction temperature of 360°–380°C. resulted in a 12% yield of citraconic anhydride.

Comparable results are observed when the feeds are adjusted to give a vapor mixture containing 0.1 percent alcohol, a contact time of 5 seconds and a reaction temperature of 250°–270°C.

EXAMPLE 4

A catalyst was prepared from a mixture of 97 percent by weight of vanadium pentoxide and 3 percent phosphorus pentoxide in a manner similar to that described in Example 3. This catalyst was charged to a tubular aluminum reactor as in Example 3 and a mixture of air and 3-methyl-3-buten-1-ol containing 1.3 molar percent of the alcohol was fed to the reactor allowing a contact time of 0.9 second. At a reaction temperature of 395°–425°C., an 8% yield of citraconic anhydride was observed.

When the conditions were adjusted to give a 0.22 percent alcohol vapor concentration, a 1.9 second contact time, and a 280°–300°C. reaction temperature, a 14% yield of citraconic anhydride was observed.

Citraconic anhydride is also obtained when conditions are further adjusted to provide a feed containing 5 percent alcohol, a 0.2 second contact time, and a 500°C. reaction temperature.

EXAMPLE 5

A catalyst was prepared from a mixture of vanadium pentoxide containing 3 percent by weight of chromic oxide using the method described in Example 3. This catalyst was tested in the oxidation of 3-methyl-3-buten-1-ol as in Example 3. Conditions and results are recorded in the following table:

| vapor conc. (%) | contact time (sec.) | bath temp. (°C.) | stoic. yield citraconic anhydride (%) |
|---|---|---|---|
| 1.3 | 0.9 | 350–370 | 8 |
| 0.22 | 1.9 | 280–320 | 12 |

Suitable catalysts may also be prepared in the same way from vanadium pentoxide alone or in combination with boric oxide, silver oxide or tungstic oxide.

EXAMPLE 6

The catalyst of Example 1 was charged to a tubular aluminum reactor as in Example 3. Air and 3-methyl-3-buten-1-ol were so fed to the reactor as to provide an alcohol vapor concentration of 1.3 percent and a contact time of 0.9 second. At a reaction temperature of 385°–410°C., a 9% yield of citraconic anhydride was observed. Adjustment of conditions to give an alcohol vapor concentration of 0.22 percent and a 1.9 second contact time at 330°–360°C. likewise provided a 9% yield of citraconic anhydride.

The vapor stream from the reactor is passed countercurrent to water in a scrubber operating at 60°C. in which the citraconic anhydride is hydrolyzed to citraconic acid and removed as a solution in the exit water stream.

EXAMPLE 7

The procedure of Example 3 is repeated except that a mixture of 5 percent oxygen and 95 percent nitrogen is substituted for the air. At a 1.3 percent molar concentration of 3-methyl-3-buten-1-ol, a 0.9 second contact time and a 320°–360°C. reaction temperature, a significant quantity of citraconic anhydride is produced. Comparable results are obtained when a 1:1 mixture of oxygen and nitrogen is substituted for the above 5:95 mixture.

The citraconic anhydride in the exit stream from these reactions is recovered as the liquid anhydride by condensation in an indirect condenser operating at about 125°C. and atmospheric pressure.

What is claimed is:

1. A process for preparing citraconic anhydride comprising contacting a gaseous mixture of a methyl butanol or a methyl butenol and oxygen with vanadium oxide at a temperature of from about 250° to 500°C, said methyl butanol and methyl butenol being 2-methyl-1-butanol, 2-methyl-2-butanol, 2-methyl-3-butanol, 2-methyl-4-butanol, 2-methylene-1-butanol, 2-methyl-2-buten-1-ol, 2-methyl-3-buten-1-ol, 2-methyl-3-buten-2-ol, 3-methyl-2-buten-1-ol, 3-methyl-3-buten-1-ol, 3-methyl-3-buten-2-ol or a mixture thereof.

2. The process according to claim 1 wherein said methyl butanol is 2-methyl-2-butanol.

3. The process according to claim 1 wherein said methyl butenol is 2-methyl-3-buten-2-ol.

4. The process according to claim 1 wherein said methyl butenol is 3-methyl-3-buten-1-ol.

5. The process according to claim 1 wherein the vanadium oxide also contains at least one oxide of phosphorus, boron, copper, silver, chromium, molybdenum or tungsten, or at least one compound convertible thereto under said process conditions.

6. The process according to claim 1 wherein said contacting continues for from about 0.2 to 5 seconds.

7. The process according to claim 6 wherein the alcohol concentration of said gaseous mixture ranges from about 0.1 to 5 percent by volume and the oxygen concentration of said mixture ranges from about 5 to 50 percent by volume.

8. A process for preparing citraconic anhydride comprising contacting a mixture of about 0.5-2 percent by volume of 2-methyl-3-buten-2-ol vapor in air with vanadium oxide at a temperature of about 320°–420°C. for a period of about 1–2 seconds.

* * * * *

UNITED STATES PATENT AND TRADEMARK OFFICE
CERTIFICATE OF CORRECTION

PATENT NO. : 3,932,469
DATED : January 13, 1976
INVENTOR(S) : Rudolph G. Berg et al It is certified that error appears in the above—identified patent and that said Letters Patent are hereby corrected as shown below:

Column 1, line 5 change "catalytic" to --invention--.

Column 1, line 6 "catalyst" should be --catalytic--.

Column 1, line 22 after "vapor" insert --phase--.

Column 2, line 30 change "ate" to --are--.

Column 2, line 53 change "LA 40" to --LA 3032--.

Signed and Sealed this twenty-second Day of June 1976

[SEAL]

Attest:

RUTH C. MASON
Attesting Officer

C. MARSHALL DANN
Commissioner of Patents and Trademarks